United States Patent [19]

Lobarev et al.

[11] Patent Number: 5,131,409
[45] Date of Patent: Jul. 21, 1992

[54] DEVICE FOR MICROWAVE RESONANCE THERAPY

[76] Inventors: Valery E. Lobarev, ulitsa marshala Grechko, 12, kv. 79; Sergei P. Sitko, ulitsa Semenovskaya, 11, kv. 64; Vadim V. Ljubchenko, ulitsa Gogolevskaya, 1, korpus 3, kv. 90, all of Kiev, U.S.S.R.

[21] Appl. No.: 681,692

[22] Filed: Apr. 8, 1991

[51] Int. Cl.$^5$ .................. A61N 1/00; A61N 2/08
[52] U.S. Cl. .................. 128/804; 343/767
[58] Field of Search .............. 128/804, 907; 343/767, 343/771

[56] References Cited

U.S. PATENT DOCUMENTS

| 676,332 | 6/1901 | Marconi | 343/749 |
| 2,642,529 | 6/1953 | Frankel | 343/767 |
| 4,334,229 | 6/1982 | Boblett | 343/767 |

Primary Examiner—Kyle L. Howell
Assistant Examiner—Scott R. Akers
Attorney, Agent, or Firm—Beveridge, DeGrandi & Weilacher

[57] ABSTRACT

The device in accordance with the invention is an apparatus for producing electromagnetic radiation for use in microwave resonance therapy. This device provides improved selectivity of the effect produced by electromagnetic radiation in the EHF band on biologically active points. The device is well suited for production by simplified mass production techniques. A continuous spectrum of electromagnetic energy in the EHF band is produced by the device, whose input is connected to a power source via a pulsed voltage generator. The output is connected to a radiating antenna. The source of the electromagnetic radiation and the radiating antenna are integrated together via a slotted transmission line. One of the ends of the slotted transmission line carries a spark discharge source which is connected to the pulsed voltage generator. The other end of the slotted transmission line serves as the radiating antenna.

12 Claims, 5 Drawing Sheets

DEVICE FOR MICROWAVE RESONANCE THERAPY

BACKGROUND OF THE INVENTION

The invention relates to the construction of appliances for microwave resonance therapy making use of electromagnetic noise waves in the EHF range (EHF-noise). Such appliance can find application in clinical and outpatient practice, as well as for needs of emergency medical service as a means for analgesia and arresting the attacks of chronic diseases, for treatment of predominantly functional disturbances of the sleep, motoricity, speech function, and so on, and for treatment of organic lesions, preferably of a psychogenic nature, e.g., peptic ulcers of the stomach and duodenum, by selective action on the nearby biologically active points (hereinafter abbreviated as "BAP").

Appliances such as the one described above must be, from an engineering standpoint, space-saving, simple in manufacture and operation, and highly reliable. From a medical viewpoint, the appliance must be capable of generating EHF-signals within a wide frequency range, with a relatively uniform spectral density of noise power and a sharp diagram of directivity of electromagnetic radiation for selective action on the nearby BAP.

Separate fulfillment of such requirements with due account of up-to-date means for generating electromagnetic radiation offers no substantial difficulties.

For instance, it is known from "Diagnostic and Therapeutic Apparatus for Reflexotherapy and Biophysical Diagnosis Methods," 1983, Moscow, in: "Low-Intensity Laser Radiations in Biology and Medicine," by V. M. Iniushin, pp. 142-145 (in Russian), about the application of He-Ne lasers for practicing reflexotherapy involving selective delivery of luminous radiation to individual BAP.

It is common knowledge that therapeutic efficacy of laser acupuncture is lower than that attained when using millimetric wave electromagnetic radiation, which is due to a fundamental difference between the aforesaid kinds of therapy. The difference resides in that when BAPs are exposed to the effect of millimetric wave radiation, there occurs a resonance interaction of the organism with a radiation source (cf. Bulletin No. 1 of the USSR Academy of Sciences, 1985, Moscow, "Response of Human Organism to EHF-radiation Electromagnetic Fields," Ye. A. Andreev, M. U. Bely, S. P. Sitko, pp. 24-32 (in Russian), whereas no resonance effect is observed when using optical-range radiation (laser acupuncture) (cf. Application of Low-intensity EHF Electromagnetic Radiation in Biology and Medicine, 1985, Publishing House of the Institute of Radioelectronics of the USSR Academy of Sciences (Moscow), "Physical Essentials of Bioresonance Correction of Physiological Status of Human Organism," by Ye. A. Andreev, M. U. Bely et al., pp. 58-83 (in Russian)).

For the reasons stated above, there are found still larger applications in the practice of reflexodiagnosis and reflexotherapy, for EHF electromagnetic radiation generators operating within the millimetric wave band, predominantly within 25 and 180 GHz.

It should be distinguished from such appliances most completely satisfying the aforesaid medicoengineering requirements, those on the base of low-power EHF-noise generators which generate an output radiation having a power by two or three orders lower than that necessary to effect a thermal action upon BAP within the aforesaid entire frequency bandwidth, or a substantial portion thereof.

The closest to the proposed invention is an appliance for microwave resonance therapy as per application Ser. No. 348,954, dated May 8, 1989 for a U.S. utility patent.

The aforesaid appliance has a generator made in the form of a source of impulse EHF-noise and connected to the input of the power supply unit through a pulsed voltage generator, while its output is connected to a radiating antenna through a high-pass filter with a mode transformer.

It is adopted in the present description of the invention that the term "EHF-noise" means "a continuous frequency spectrum EHF electromagnetic radiation."

The appliance discussed above is a very space-saving one, that is, it has overall dimensions close to those of a gas-fired electric lighter, is very economic as to costs of the process equipment, simple to manufacture and operate, and reliable in use. With this appliance, it is possible to generate electromagnetic radiation within a wide frequency bandwidth with a relatively uniform spectral density of noise power ($\pm 20$ percent of the average density) throughout the working frequency bandwidth.

The appliances with the characteristics set forth above are capable of cutting down the time spent carrying out a treatment procedure and reducing a total absorbed radiation dose due to dispensing with the procedure of searching for resonance therapeutic frequencies.

However, the topology of the biologically active points on the patient's body is such that the points are situated very close to one another in a plurality of the patient's body areas. Thus, for instance, over a hundred of the BAP are located on the auricular concha so that when using the known appliance, a selective effect produced on every particular BAP in the area cannot at all times be attained. One of the causes of this is a comparatively large diameter of the radiation spot applied to the body surface. Besides, when employing an improved method of action specifying a definite sequence of actions on the nearby BAP, such as the auricular ones, the problem of how to increase this selectivity of action becomes still more important. Taking due account of the fact that further BAP are found in the course of development of reflexotherapy, providing a device that meets the requirements set forth hereinabove is made still more necessary.

It is worth noting that the problem of how to simplify the manufacturing technology of the known appliance becomes more important under conditions of mass production thereof. First and foremost, it is required to eliminate manual assembly and adjusting of the principal units, that is, the waveguide, mode transformer, and a spark discharge gap proper as a source of EHF-noise.

As the diagnostic and other information is accumulated on the modes of action produced by electromagnetic radiation in the EHF band, necessity arises to differentiate the frequency spectrum of the emitted power depending on the kind of pathology, i.e., to eliminate the disadvantage inherent in the prototype, a failure to provide a possibility of setting a desired frequency band of the output radiation in the course of manufacture of the appliance. The filter provided in the prototype is essentially a low-pass filter which features a single cutoff frequency corresponding to the lower limit of the EHF band.

The use of a constructionally separated mode transformer and radiating antenna cannot be considered as a construction improvement feature.

SUMMARY OF THE INVENTION

It is a primary and essential object of the invention to provide a device for microwave resonance therapy which provides a highly selective therapeutic effect on the nearby biologically active body points on the patient.

It is another object of the invention to provide a device for microwave resonance therapy, which is featured by a simpler construction.

It is one more object of the present invention to provide a device for microwave resonance therapy having a more technologically perfect construction dispensing with manual assembly and adjustment of the device.

The foregoing and further objects are accomplished by providing, in a device for microwave resonance therapy, a source of electromagnetic radiation with a continuous frequency spectrum in the EHF band, the source having a radiating antenna connected with its input through a pulsed voltage generator, to a power source. In accordance with the invention, the source of electromagnetic radiation with the radiating antenna is shaped as a slotted transmission line having two ends, at one end, a spark discharge source is situated, and at the other end, a radiating antenna is provided.

This construction arrangement of the device provides for a selective effect of electromagnetic radiation on the BAP and is a fundamental solution that assures the achievement of further objects of the invention.

It is expedient that a cylindrical slotted line be used as a radiation source and a radiating antenna, wherein a conducting member serves as one of the electrodes, while an additional electrode serves as a second electrode, wherein the second electrode is situated close to one of the ends of the cylindrical slotted line in the neighborhood of the slot so as to establish a spark discharge gap with the faces of the slot, and the other end of the line serves as a radiating antenna.

Extended capabilities for adjusting the spark discharge gap for size is attained in an embodiment of the invention, according to which the electric conducting member of the cylindrical slotted line has a thicker portion at one of its ends smoothly joined together with the rest of the conducting member, the outer edges of the slot smoothly diverging in the area of transition to the thicker portion of the conducting member, while the additional electrode is disposed in a thinner portion of an electric drive for adjustment movement with respect to the slot.

One of the most efficient embodiments of the invention is the one, wherein the radiating antenna is in fact a smooth divergence of the slot toward the end opposite to the area of location of the additional electrode.

In an alternative embodiment of the invention, the radiating antenna is essentially a flat end of the cylindrical slotted line, symmetrical with respect to the slot and so inclined that the slot length is shorter than the length of the cylindrical slotted transmission line.

One of the distinguishing features of the device resides in the fact that the radiating antenna is accommodated in the cylindrical waveguide coaxially therewith and arranged with a radial clearance to the latter.

One more embodiment of the invention is featured by considerable simplicity, according to which a cylindrical slotted line is used as a radiation source and a radiating antenna, wherein the cylindrical slotted line includes an electric conducting member composed of two electrically insulated halves separated by longitudinal slots, while the spark discharge source is shaped as oppositely arranged projections on the faces of one of the slots establishing a spark discharge gap.

A substantially simplified manufacturing technology of the device is attainable when using a planar slotted line as a radiation source, the slotted line having an electrically conducting member including metallic plates situated side-by-side and separated by a slot, while the spark discharge gap is shaped as a pair of oppositely arranged projections located on the respective faces of the metallic plates and forming a spark discharge gap.

Maximum sharpness of the directivity diagram of the radiating antenna can be attained when the antenna additionally includes a dielectric rod having a pointed end and situated on the metallic plates in such a manner that its pointed end extends beyond the end of the planar slotted transmission line.

An extended service life of the device can be attained when the planar slot line is provided with a hermetic casing.

One more feature of the device inlcudes having the hermetic casing filled with an inert gas or some other controlled atmosphere.

BRIEF DESCRIPTION OF THE DRAWINGS

In what follows, the invention is illustrated by a detailed description of some exemplary embodiments thereof with reference to the accompanying drawings, wherein.

DETAILED DESCRIPTION OF THE INVENTION

Figure 1:
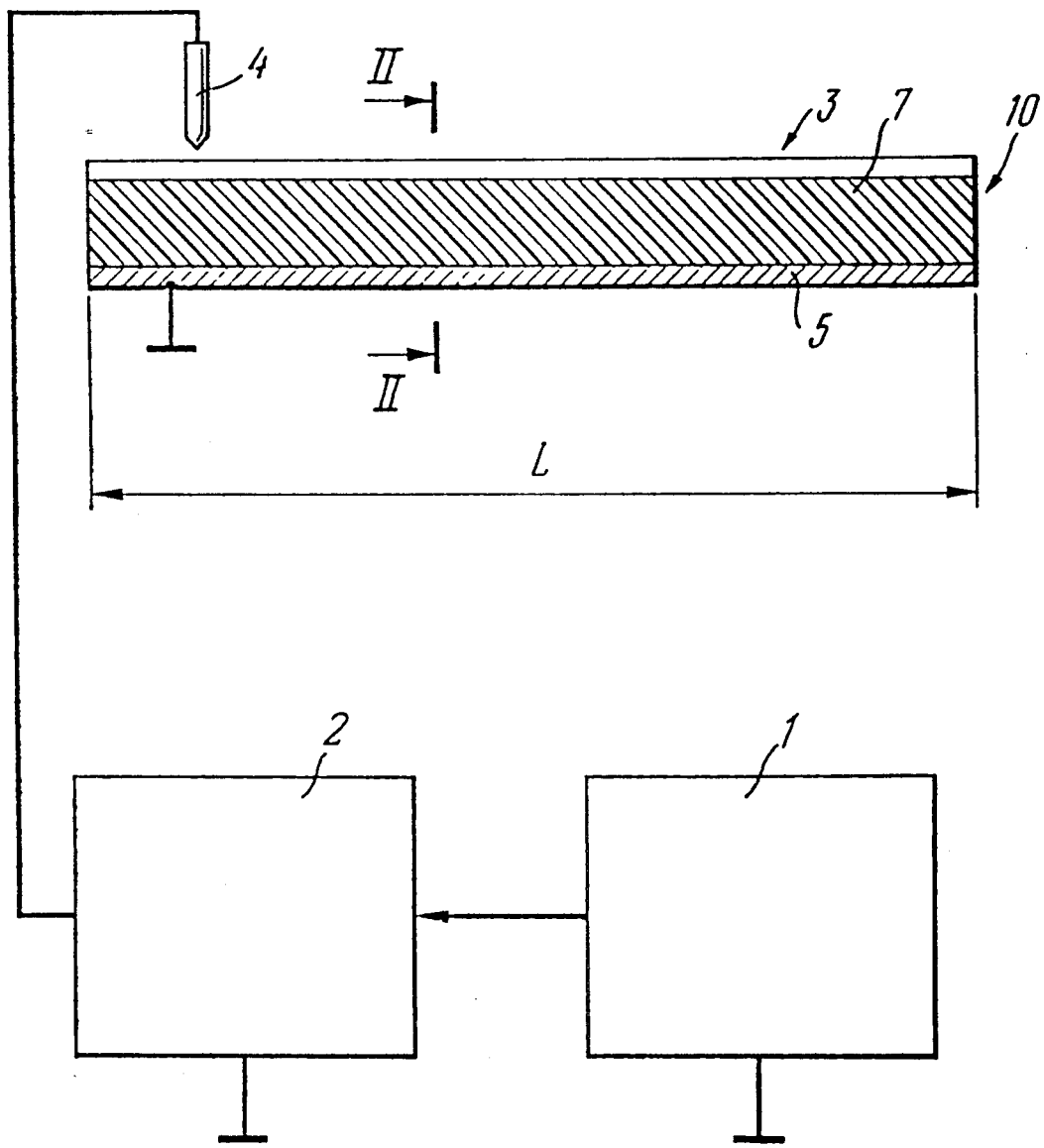
FIG. 1 is an axially sectional view of a device, according to the invention, showing a power source.
Figure 2:
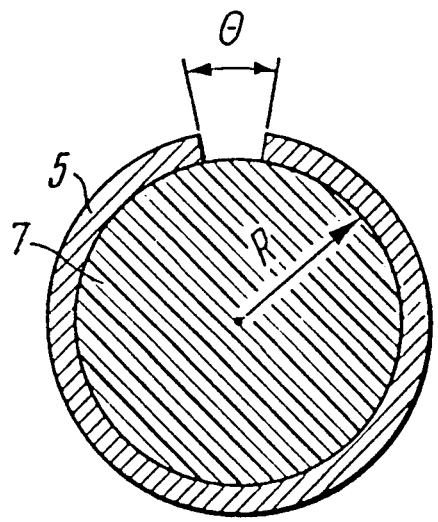
FIG. 2 is a sectional view taken on the line II—II in FIG. 1.

According to one of the embodiments of the invention, as shown in FIG. 1, the device for microwave resonance therapy comprises a power source 1 to whose output is connected a pulsed voltage generator 2, a cylindrical slotted transmission line 3, and a needle-like element 4 serving as one of the electrodes.

The power source 1 used in accordance with the invention may be a storage cell, a storage battery, or a power main. The pulsed voltage generator 2 may be provided in a commonly known way as a blocking oscillator with an interrupter and a step-up pulsing transformer at the output. The output pulses of the generator 2 should have an energy on the order of tens of millijoules.

The cylindrical slotted transmission line 3 has two ends and comprises a hollow cylindrical conducting member 5 having a longitudinal slot 6 filled with a dielectric. The dielectric may be air at the least, although some other dielectrics may also be used, such a non-Newtonian fluids featuring relatively high shear strength which prevents their escape under the gravitational field of the Earth. More particularly, plastisols and plastigels based on polar and non-polar polymers may be used. Solid dielectrics, preferably solids such as quartz, sapphire, and more complex ceramic material based thereon, or pure polymers, such as polytetrafluoroethylene, such as TEFLON (a trademark of the E.I. Dupont de Nemours Co.) may also be used.

The length L of the cylindrical slotted transmission line, the angular dimension $\Theta$ of the slot, the inside radius R and the permittivity $\xi$ of a dielectric 7 can assume the following values: L=15 to 40 mm, $\Theta$=15° or 16°, R=0.34 to 0.36 mm, $\xi$=2.0 to 2.4.

Figure 3:
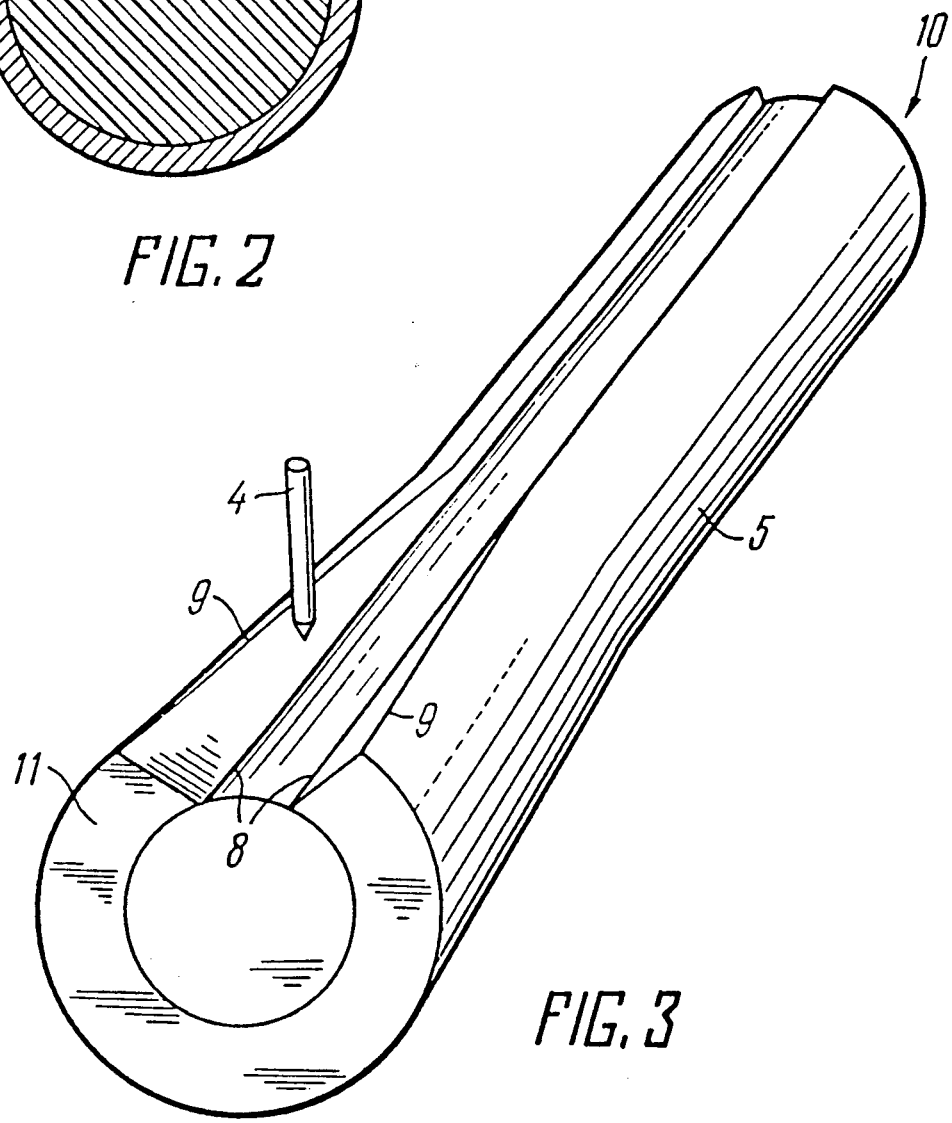
FIG. 3 is a three-dimensional view of one of the exemplary embodiments of an electromagnetic radiation source in the device, according to the invention.

The thickness of the conducting member 5 is large enough for the faces of a slot 6 to have inner and outer edges 8 and 9, respectively, as shown in FIG. 3.

The conducting member 5 serves as the other electrode, along with the needle-like electrode element 4. The electrodes 4 and 5 are connected to the unlike conductors at the output of the pulsed voltage generator 2 to form a source of spark discharge, which serves as a generator of a continuous-spectrum EHF electromagnetic radiation. With this aim in view, the needle-like element 4 is disposed close to one hollow conducting member 5 and in the vicinity of the slot 6.

According to the embodiment of the device as shown in FIG. 1, the opposite end of the cylindrical slotted transmission line 3 serves as a radiating antenna 10.

The length of the cylindrical slotted transmission line 3 and, first and foremost, the distance from the needle-like element electrode 4 to the radiating antenna 10 depends on the mode of propagation of an electromagnetic radiation wave along the cylindrical slotted transmission line 3 and is selected such as to rule out the leaky modes.

To conduct microwave resonance therapy (hereinafter abbreviated "MRT"), the power source 1 is cut in and its output voltage is applied to the input of the pulsed voltage generator 2, which may be shaped as a blocking oscillator with an interrupter and a step-up pulsing transformer at the output. The output pulses of the generator 2 must have an energy on the order of tens of millijoules. A transient spark discharge occurs in the interelectrode gap between the needle-like electrode 4 and the conducting member 5 in response to the aforementioned pulses arriving at the electrode 4. This results in electromagnetic oscillations, the greater proportion of which propagate in the shape of a slotwave toward the radiating antenna 10. Thus, an electromagnetic field is emitted by the antenna 10 into free space. A therapeutically efficient field is located at a maximum distance of 1.5 m away from the end of the cylindrical slotted transmission line 3.

According to another embodiment of the device, as shown in FIG. 3, the conducting member 5 has a thicker portion 11 smoothly joined together with the rest of the cylindrical slotted transmission line 3. The needle-like electrode element 4 is arranged in the vicinity of the thicker portion 11 of the conducting member 5. The rest of the units of this embodiment of this device are the same as in the embodiment described above in conjunction with FIG. 1.

The outer edges 9 of the slot 6 smoothly diverge in the area of a smooth changeover to the thicker portion 11 of the conducting member 5.

The aforedescribed construction arrangement of the slot 6 makes it possible, on the one hand, to simplify requirements relating to the dimensions of the needle-like element-electrode 4 and to the size of an interelectrode or spark gap. Furthermore, this arrangement enables one to provide optimum matching of the needle-like element electrode 4 with the cylindrical slotted transmission line 3, whereby the maximum amplitude of electromagnetic oscillations falls at the radiating antenna 10.

Figure 4:
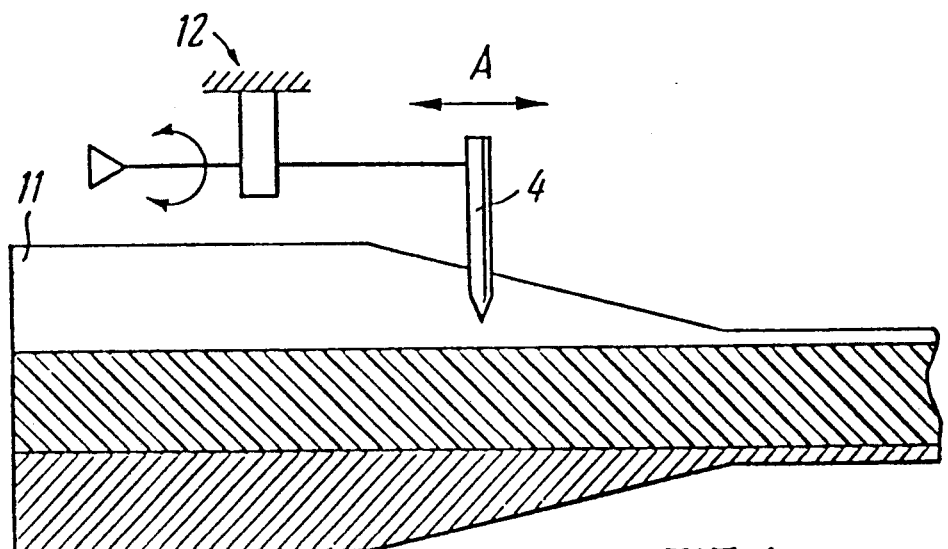
FIG. 4 is a sectional view of an embodiment of an electromagnetic radiation source.

FIG. 4 illustrates one more embodiment of the invention according to which the needle-like element electrode 4 is provided with a drive for adjusting the movement of the needle-like electrode 4 with respect to the slot 6. In this embodiment, the needle-like element electrode 4 is linearly movable along the direction of arrow A with the aid of a micrometer screw 12. Some other modifications of the drive and of the electrode shape are also possible; for instance, the electrode 4 may be shaped as a flat eccentric set on a shaft and adapted to engage the slot 6.

Figure 5:
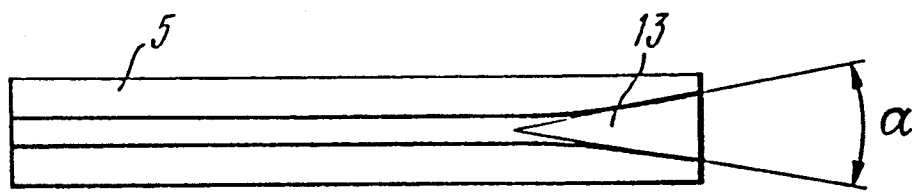
FIG. 5 is an embodiment of a radiating antenna.

FIG. 5 presents still one more embodiment of the device, according to which there is a modification of the radiating antenna 10. According to this embodiment, the radiating antenna is shaped as a smooth divergence 13 of the slot 6 toward the end opposite the location of the needle-like element electrode 4. Such an embodiment enables one to attain optimum matching of the cylindrical slotted transmission line 3 with free space by appropriately changing the angle $\alpha$ of the slot divergence. Thus, for instance, with the angle $\alpha$ ranging within 15 and 120 degrees, there is ensured maximum transmission of energy of an electromagnetic wave propagating along the slotted transmission line 3 into free space toward the patient's skin.

Figure 6:
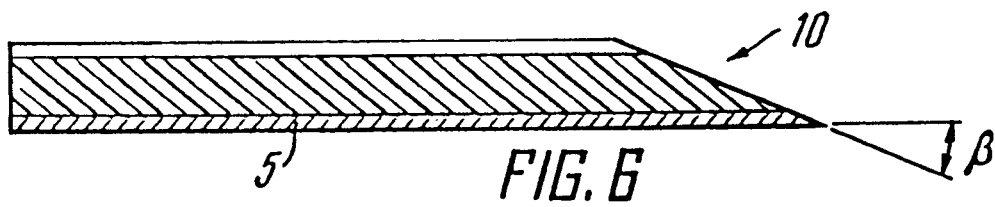
FIG. 6 is another embodiment of a radiating antenna.

Another embodiment of the radiating antenna 10 is presented in FIG. 6, wherein the radiating antenna 10 is shaped as a flat inclined end of the cylindrical slotted transmission line 3, this end being opposite to the place where the needle-like element electrode 4 is situated. The bevelled end is symmetrically arranged with respect to the slot 6 and the angle $\beta$ of its incline toward the horizontal plane is in fact an acute angle, i.e., the length of the slot 6 is shorter than the length of the cylindrical slotted transmission line 3. An optimum value of the angle can be assumed as being within the range of 20 and 35 degrees when the dielectric permittivity $\xi$=2.2.

Figure 7:
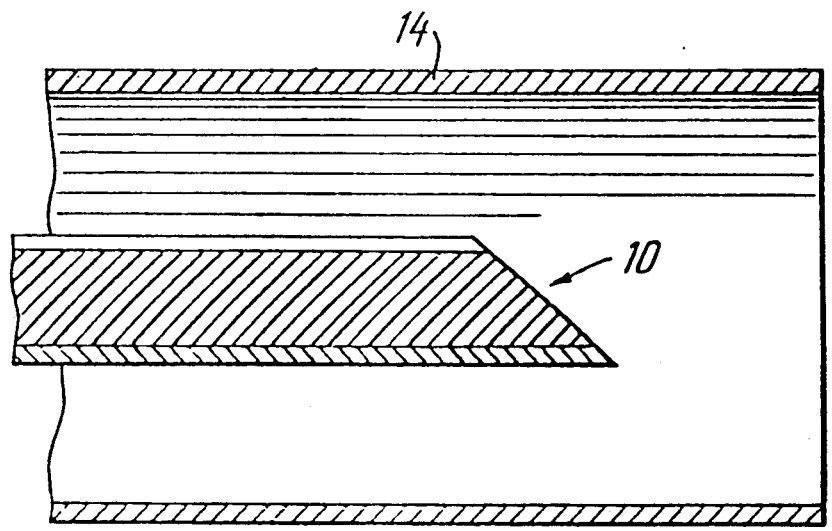
FIG. 7 is a further embodiment of a radiating antenna.

According to an embodiment of the device shown in FIG. 7, the radiating antenna 10 is concentrically enclosed with a cylindrical waveguide 14 whose inside diameter is greater than the outside diameter of the cylindrical transmission line 3. Whenever necessary, the waveguide 14 may be provided with a drive for adjusting its movement along the cylindrical slotted transmission line 3. This movement is aimed at ensuring operation of the device in the leaky modes in cases when the length L of the slotted transmission line is to be increased, as well as for setting the range of the output radiation wavelengths.

Figure 8:
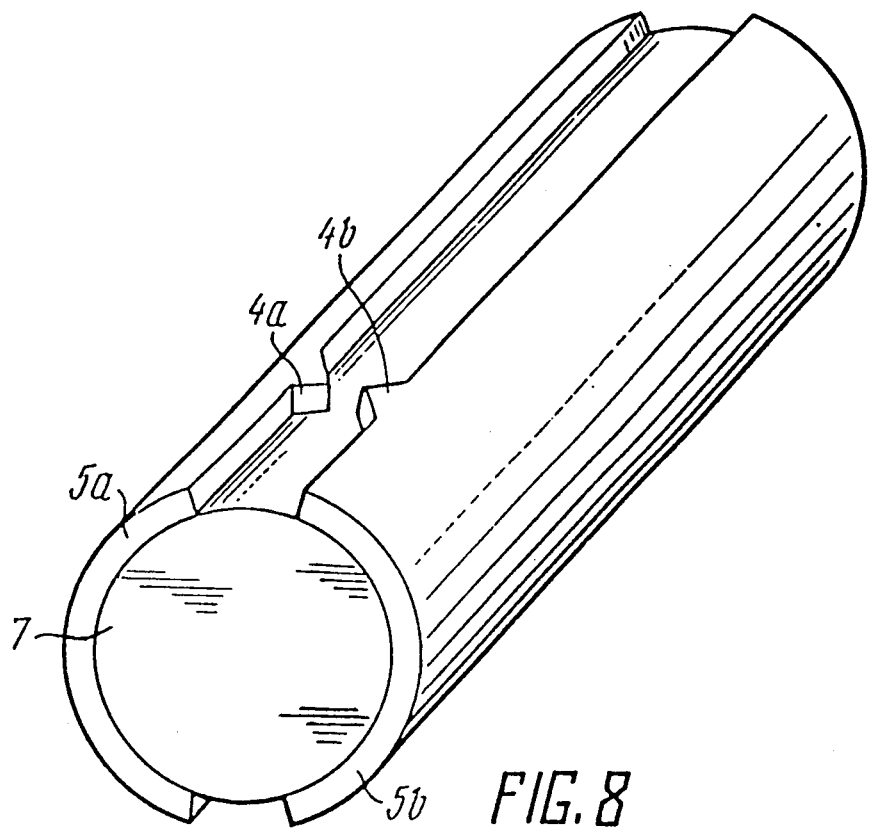
FIG. 8 is a three-dimensional view of one more embodiment of an electromagnetic radiation source.

In the embodiment of the device as represented in FIG. 8, which device is used as an electromagnetic radiation source and a radiating antenna, the cylindrical slotted transmission line 3 includes a conducting member which is separated along the generatrix into the electrically insulated halves 5a and 5b. The oppositely arranged projections 4a, 4b of the respective halves 5a and 5b are employed as the electrodes in this embodiment.

Like in the embodiments described above, the projections 4a and 4b are situated at the end of the transmission line opposite to the radiating antenna 10. According to this embodiment, the output of the pulsed voltage generator 2 is connected to the halves 5a and 5b of the conducting element. A spark discharge gap is defined by the projections 4a and 4b. The herein-described embodiment makes is possible to extend the range of the output radiation due to "a second" slot, which, in this case, may have geometric dimensions different from those of "a first" slot. In addition, the production technology of the device according to this embodiment is simpler, since instead of a separate element, that is, the electrode 4, the function of the electrode 4 is performed by the projections 4a, 4b of the halves of the conducting member 5a, 5b.

Figure 9:
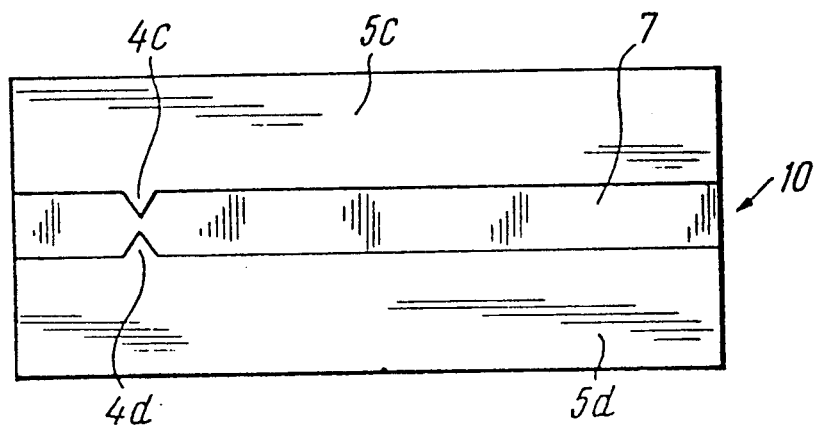
FIG. 9 is an embodiment of a planar source of electromagnetic radiation.

The simplest production technology of the device can be realized when using, as the radiation source, a planar slotted line as shown in FIG. 9. The parallel metallic plates 5c and 5d are put on a dielectric backing using any known technique. The plates 5c and 5d are equivalent to the halves of the conducting member 5a and 5b in the embodiment of the device shown in FIG. 8. The projections 4c and 4d provided on the plates are used as the electrodes, or else rods made of a refractory metal, such as tungsten, and secured to the plates may be used (not shown).

In this embodiment, the opposite end of the planar slotted transmission line can also be used as the radiating antenna.

Figure 10:
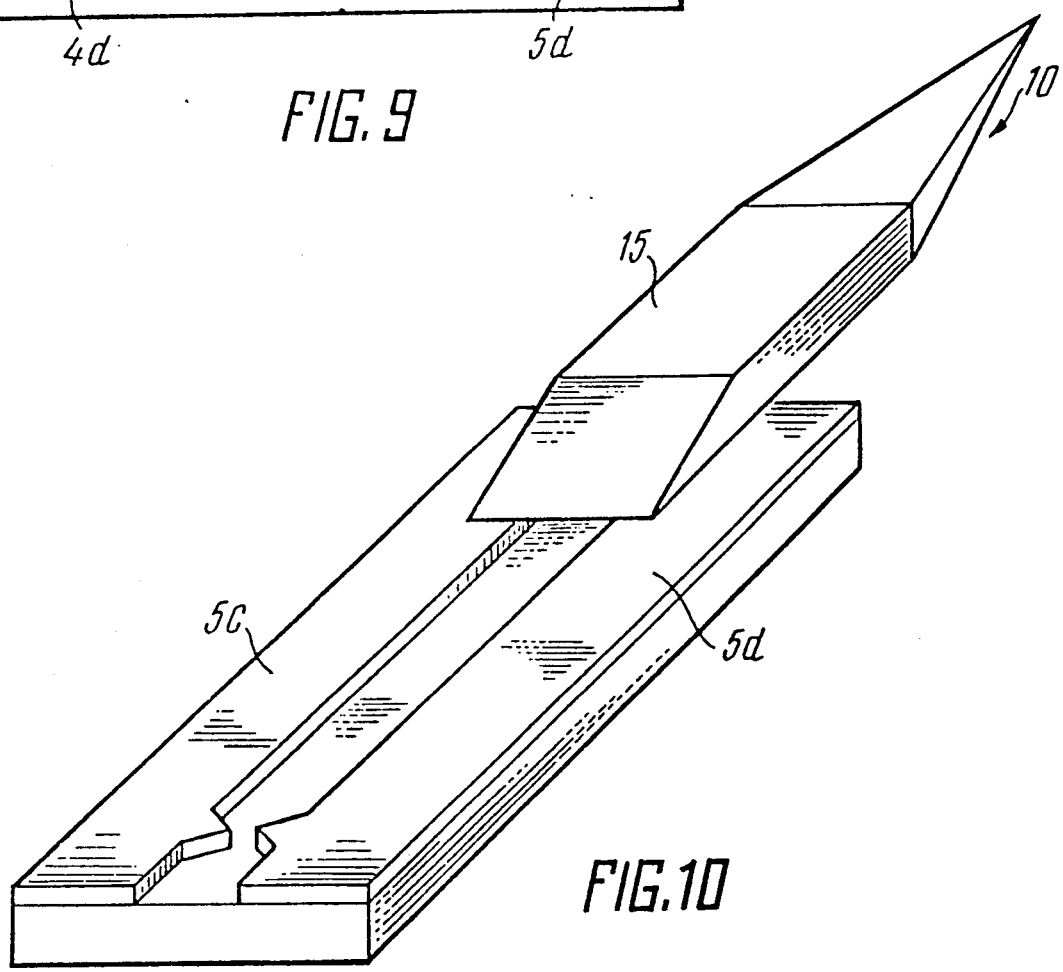
FIG. 10 is a further embodiment of a planar source of electromagnetic radiation.

There is one more embodiment of the radiating antenna 10 described herein, wherein the antenna includes additionally a dielectric rod 15, as shown in FIG. 10, situated on the plates 5c and 5d and having a pointed end that extends beyond the emitting end of the antenna.

It is expedient that the planar slotted line be enclosed in a hermetic casing (omitted in the drawings), which enables one to extend the service life of the device. Furthermore, filling the casing with an inert gas is instrumental in changing the permittivity value of the slot, which in turn makes it possible to modify the range of the output radiation wavelengths. Such a gas may be considered as optimum if it includes the presence of resonance transitions in the EHF band.

Given below are exemplary case histories to illustrate the practical application of the above-described device for treating patients suffering from certain kinds of widespread diseases of the emotional-motivation realm of human beings.

EXAMPLE 1

Microwave resonance therapy with the aid of the device in accordance with the invention was applied to male patient V., born 1954, a worker who suffered from chronic alcoholism (dipsomania) from 1980. The patient consumed alcoholic beverages permanently, four to six times a week. He exhibited a high tolerance to alcohol. A treatment course comprising 10 sessions was instituted, the treatment being given on an outpatient basis.

During the first treatment session, the patient developed a state of alcoholic intoxication, which was a favorable prognostic symptom. After the first session, the patient ceased drinking alcoholic beverages and denied any desire or attraction for such beverage. After the fifth and sixth sessions, the patient began to note objectionable sensations in response to the odor of alcohol. After ten sessions, the patient adhered to total alcoholic abstinence for the recent 3 months.

In a given clinical case, the therapeutic effect was produced by electromagnetic radiation in the EHF band upon the auricular biologically active points of the limbic area (LS). The treatment session lasted 20 minutes. Control of the treatment efficacy was carried out by a known method based on assessment of the blood content of ethanol and acetaldehyde by the gas chromatogrophy technique. Upon completion of the treatment course, the blood content of the aforementioned substances was found to correspond to their blood level in psychically healthy individuals.

EXAMPLE 2

The device in accordance with the invention was applied for carrying out a course of microwave resonance therapy with respect to a male patient S., 7, who suffered from nocturnal enuresis since his very birthday, i.e., the child voided urine in the bed every night. Before being admitted to the clinic, the patient had been given a course of chemotherapy, he was awaken for voiding the urinary bladder. He was restricted in drinking, that is, attempts were made for treating the patient by making use of traditional methods. However, such treatments were of no effect.

A course of microwave resonance therapy containing 8 daily sessions each lasting 20 minutes was prescribed. The patient was exposed to the effect of the electromagnetic radiation emitted by the device and applied to the biologically active points on the meridian of the urinary bladder. After the fourth session, the urination frequency decreased, and the patient began to awake for urination spontaneously. His general state improved, and the patient became more quiet. By the eighth session, nocturnal urination ceased completely.

EXAMPLE 3

The device in accordance with the invention was used in a way similar to that described above with respect to a male patient A., 22, who suffered from sexual impotence. The patient was ill for a year before resorting to medical aid. The microwave resonance therapy in a given clinical case comprised 3 treatment courses comprising 10 sessions each at a monthly interval between the courses, each session lasting 20 minutes.

The electromagnetic radiation emitted by the device was applied to the auricular sexual points. During the first course (after the initial three sessions), there was noted a general rise in the patient's state, his mood improved, and a slight erection was noticed. Within the period of the second course, the patient was able to conduct a short-time coitus. After the third course of treatment, the patient was able to conduct a normal sexual life. The patient got married.

Stated above are the embodiments of the invention actually used in clinical trials. At the present time, this device passes clinical trials for treatment of patients with diseases of the gastroduodenal region, the locomotorium, etc.

An indisputable advantage inherent in the present device, unlike the known devices of the same character, resides in its guaranteed selective effect produced by the EHF-band electromagnetic radiation on nearby biologically active points, such as those located on the ear.

We claim:

1. A device for microwave resonance therapy comprising:
   a power source;
   a pulsed voltage generator connected to the power source and having an output;
   a slotted transmission line for transmitting electromagnetic waves of an EHF range, said slotted transmission line including a conducting member defining a longitudinal slot having a first end and a second end;
   a spark discharge source for generating a continuous frequency spectrum electromagnetic radiation including radiation in the EHF range when a spark discharge exists, said spark discharge source being at the first end of the slotted transmission line adjacent the slot and including a first electrode and a second electrode, said first and second electrodes defining a spark gap and being connected to the output of the pulsed voltage generator, wherein at least one of the first and second electrodes forms the conducting member of the slotted transmission line; and
   a radiating antenna formed at the second end of the slotted transmission line.

2. A device as claimed in claim 1, wherein the conducting member of the slotted transmission line defines a hollow and cylindrical tube which is filled with a dielectric material, and the spark discharge source includes a portion of the hollow cylindrical conducting member as the first electrode; the second electrode being in a needle-like electrode form; and the radiating antenna being an end face of the hollow cylindrical conducting member at the second end of the slotted transmission line.

3. A device as claimed in claim 2, wherein the hollow cylindrical conducting member includes a thick portion at the first end thereof, wherein the thick portion smoothly joins with a thin portion at the second end of the conducting member; the conducting member having outer edges defining the longitudinal slot, wherein the outer edges smoothly diverge forming the thick portion of the hollow cylindrical conducting member toward the first end of the slotted transmission line; and the needle-like electrode being provided with a drive means for adjusting the position of the needle-like electrode along the slot.

4. A device as claimed in claim 2, wherein the radiating antenna includes a portion of the slot formed by outer edges of the hollow cylindrical conducting member, wherein the outer edges of the conducting member at the second end thereof smoothly diverge toward the end face of the hollow cylindrical conducting member.

5. A device as claimed in claim 2, wherein the radiating antenna has a flat and slanting end face arranged symmetrically with respect to the longitudinal slot in the hollow cylindrical conducting member, wherein the longitudinal slot is shorter than the cylindrical conducting member.

6. A device as claimed in claim 2, further comprising a cylindrical waveguide, wherein the radiating antenna is arranged coaxially within the waveguide and radially spaced from the waveguide.

7. A device as claimed in claim 1, wherein the conducting member of the slotted transmission line defines a hollow, cylindrical tube, said tube being filled with a dielectric material, and the conducting member defining a second longitudinal slot, thereby providing two separate sections of the hollow cylindrical conducting member; the first and the second electrodes being oppositely arranged projections on edge portions of the conducting members such that the projections project into the at least one of said longitudinal slots.

8. A device as claimed in claim 1, wherein the conducting member of the slotted transmission line is a planar member which includes at least two metallic plates attached to a dielectric plate, wherein each conducting member includes a side surface and the conducting members are arranged in a spaced side-by-side relationship with respect to one another, and the spark discharge source includes a pair of opposing projections, one projection being on each side surface of the metallic plates, whereby the spark gap is defined between the opposing projections.

9. A device as claimed in claim 8, wherein the radiating antenna further comprises a dielectric rod member having a pointed end portion, said dielectric rod being arranged on the metallic plates such that the pointed end portion thereof extends beyond the second end of the slotted transmission line.

10. A device as claimed in claim 9 further comprising a hermetic casing which encloses the slotted transmission line.

11. A device as claimed in claim 10, wherein the hermetic casing is filled with an inert gas.

12. A device according to claim 2, further comprising a drive means for adjusting the position of the needle-like electrode.

* * * * *